(12) United States Patent
Kerr

(10) Patent No.: US 8,617,464 B2
(45) Date of Patent: *Dec. 31, 2013

(54) SANITIZING DEVICES AND METHODS OF THEIR USE

(75) Inventor: James Kerr, Old Orchard Beach, ME (US)

(73) Assignee: RJG Associates, LLC, Port St. Lucie, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/344,076

(22) Filed: Jan. 5, 2012

(65) Prior Publication Data

US 2013/0177474 A1 Jul. 11, 2013

(51) Int. Cl.
*A61L 2/10* (2006.01)

(52) U.S. Cl.
USPC .............................................. 422/24; 422/22

(58) Field of Classification Search
None
See application file for complete search history.

(56) References Cited

U.S. PATENT DOCUMENTS

| | | | | |
|---|---|---|---|---|
| 4,112,124 | A * | 9/1978 | Jarvis | 426/234 |
| 4,425,677 | A | 1/1984 | Cox | |
| 4,866,805 | A | 9/1989 | Oden et al. | |
| 4,922,578 | A | 5/1990 | Miettinen | |
| 5,071,628 | A | 12/1991 | Alazet | |
| 5,297,309 | A | 3/1994 | Rotoli | |
| 5,950,269 | A | 9/1999 | Openshaw et al. | |
| 6,146,588 | A | 11/2000 | Deighton | |
| 6,165,526 | A * | 12/2000 | Newman | 426/248 |
| 6,651,288 | B1 * | 11/2003 | Hackett | 15/104.92 |
| 6,749,918 | B2 | 6/2004 | Staal | |
| 6,886,210 | B2 | 5/2005 | Dean | |
| 7,118,852 | B2 * | 10/2006 | Purdum | 435/2 |
| 8,143,596 | B2 | 3/2012 | Yerby | |
| 2004/0078909 | A1 | 4/2004 | Coppa | |
| 2004/0168274 | A1 | 9/2004 | Greely | |
| 2005/0160549 | A1 | 7/2005 | Dean | |
| 2007/0164232 | A1 | 7/2007 | Rolleri et al. | |
| 2008/0104782 | A1 | 5/2008 | Hughes | |
| 2009/0065716 | A1 | 3/2009 | Ullman | |
| 2010/0104470 | A1 * | 4/2010 | McCabe | 422/22 |
| 2010/0193709 | A1 | 8/2010 | Dalton | |

FOREIGN PATENT DOCUMENTS

| | | | |
|---|---|---|---|
| JP | 10052480 | * | 2/1998 |
| WO | 88/03775 | A1 | 6/1988 |
| WO | 97/28733 | A1 | 8/1997 |
| WO | 00/76388 | A1 | 12/2000 |
| WO | 00/78021 | A1 | 12/2000 |
| WO | 2009/088379 | A1 | 7/2009 |
| WO | 2009/147263 | A1 | 12/2009 |
| WO | 2009/147264 | A1 | 12/2009 |

OTHER PUBLICATIONS

English machine translation of JP 10052480 Kato et al. Feb. 1998 retrieved from Industrial Property Digital Library.*

* cited by examiner

*Primary Examiner* — Sean E Conley
*Assistant Examiner* — Donald Spamer
(74) *Attorney, Agent, or Firm* — James G. Shelnut; Joda Technologies, LLC

(57) ABSTRACT

The present invention relates to sanitization devices and methods. More particularly, the invention relates to devices and methods that significantly reduce or eliminate germs, bacteria and/or other microorganisms from objects such as bags, purses, footwear or other objects, as well as bare feet, hands, paws, hooves or other anatomical surfaces, which come into contact with them. The device and method uses germicidal radiation which exposes only the areas of the object that come into applied contact with the device. A top platform of the device is partitioned so that each partition can act independently of each other.

3 Claims, 4 Drawing Sheets

SANITIZING DEVICES AND METHODS OF THEIR USE

FIELD OF DISCLOSURE

The present disclosure relates to sanitization devices and methods. More particularly, the disclosure relates to devices and methods that significantly reduce or eliminate germs, bacteria and/or other microorganisms from objects such as bags, purses, footwear or other objects, as well as bare feet, hands, paws, hooves or other anatomical surfaces, which come into contact with them. The device and method uses germicidal radiation which exposes only the areas of the object that come into contact with the device. The device is partitioned so that each partition can act independently of each other.

BACKGROUND OF THE DISCLOSURE

Bacteria, viruses, germs, molds, fungi and other undesirable microorganisms are transferred from one area to another through contact with people, animals and objects that come into contact with them.

The present disclosure is concerned with the problem of spreading microorganisms that are carried on the outer surfaces of footwear and other objects as well as hands, feet, paws, hooves and other anatomical surfaces that have been exposed to areas contaminated with undesirable microorganisms. The outer bottom surfaces of footwear such as soles and heels can come into contact with floor areas or outdoor ground areas that may be unsanitary and contaminated with microorganisms such as bacteria, viruses, germs molds, and fungi. Areas where such microbial contamination commonly exists include hospital areas, such as emergency rooms, food handling areas such as food markets, restaurants, recycling areas, and refuse dumps as well as public toilets, public sidewalks and streets, handrails on staircases and escalators, parks, park benches, farms, or anywhere that the public frequents. Someone or something that has been contaminated with an undesirable microorganism can easily and unknowingly spread the microorganisms around. In some cases the contamination can result from urine in areas near public toilets and urinals, animal urine and feces as well as human sputum on sidewalks, streets, lawns, etc.

The outer surfaces of other objects such as suitcases, handbags, purses, briefcases, packages, and the like which come into contact with such contaminated areas as airport bathrooms, bars, and restaurants which may expose them to domestic and international microorganisms also become contaminated and thereby become a source of further microbial contamination. Thus, footwear and other objects can carry microorganisms into the home, office, car or other personal areas.

Further, house pets that have come into contact with contaminated areas such as parks, yards, and the like can also carry undesirable microorganisms into the home. In livestock areas cattle, horses, sheep and the like constantly come into contact with undesirable microorganisms and spread them around on the paws, hooves or feet.

In all these scenarios, a person's hands may also become contaminated by touching a contaminated area. This will result in the transfer of the pathogenic microorganisms into the body through subsequent touching of the mouth, eyes, ears, and such. Similarly, bare feet can be exposed to microorganism contamination when walking bare foot outside or in locker rooms, pools, showers and the like and further spread them.

It is therefore highly desirable to eliminate or significantly reduce the amounts of these microbes from surfaces that carry them.

Solutions to this problem have been disclosed whereby devices containing fluid disinfectants either wet the bottom of footwear through sponge applications or a disinfectant is sprayed onto the bottom of footwear. The solutions create other problems such as slippery soles, tracking of the fluids and potential exposure to toxic materials relating to the disinfectant. A dry method would thus be more desirable.

A device described in US Pat. Appl. 2010/0193709 utilizes a platform that is transparent to UVC sanitizing radiation uses to disinfect a shoe or foot. The transparent platform is made of glass which blocks a certain portion of the UV light with only a remainder of the light illuminating the shoe or foot. The platform may also be a metal grid allowing for the UVC light to shine through. The application also describes a cover that the feet or shoes go into so that any stray UVC light does not escape. The glass used in this application blocks the disinfecting UVC wavelength of 254 nm and allows through the non-disinfecting UVB and UVA wavelengths and is therefore not suitable for disinfecting applications. The cover in this application presents a tripping hazard as well as an imperfect cover for blocking stray UVC light.

A device described in US Pat Appl. 2010/0104470 describes a device that uses a UV light along with a platform preferably made of Plexiglas and a "soft plastic material" on top of the platform with a gel between the plastic and the Plexiglas that is absorptive of the UV light. When a shoe steps on the platform the gel will be pushed aside and the UV will shine through the Plexiglas, the "soft plastic material" and onto the sole of the shoe. Radiation with germicidal activity is 254 nm which will not pass through Plexiglas which is polymethylmethacrylate. Although the application states other transparent materials can be used for the platform, no enabling materials are described therefore leaving those skilled in the art to perform a substantial amount of research to find suitable materials. Additionally, the application states "soft plastic materials" that are substantially transparent to the disinfecting radiation can be used, without any suggestion as to what those materials might be, again leaving it to the practitioner to perform a substantial amount of research to determine a material which is soft, pliable and transparent to the disinfecting radiation, which again is 254 nm. While many gels absorb radiation there, not any gel will be suitable for this application. The gel needs to have to correct viscosity so that it will push away when pressure is applied but not be so viscous that when pressure is removed, the gel will flow back into the area creating a substantially uniform thickness ready for the next shoe to disinfect.

Thus more efficient devices and methods and more suitable materials are needed to properly eliminate or significantly reduce undesirable microorganisms. Additionally these are no provisions for hands sanitation, house pet sanitation or other animal sanitation.

SUMMARY OF THE EXEMPLARY EMBODIMENTS

It is an object of the current invention to overcome the deficiencies commonly associated with the prior art as discussed above and provide devices and methods that eliminate or significantly reduce undesirable microorganisms from objects such as bags, purses, footwear or other objects, as well as bare feet, hands, paws, hooves or other anatomical surfaces.

In one embodiment, a device is provided for the elimination or significant reduction of undesirable microorganisms from objects which contains a housing having a bottom platform, sidewalls and a top platform that encloses and is attached to the top of the housing. The top platform is partitioned into two essentially equal sections having a top layer made of a deformable UVC transparent fluorinated film, a bottom layer containing a support layer containing a number of perforation for allowing UVC light to pass through, and may optionally contain a layer of a UVC transparent material a bottom layer made from UVC transparent quartz, and sidewalls, with a UVC absorbent liquid contained in the top platform between the top layer and the bottom layer. The device has one or more UVC emitting devices situated in the housing, between the bottom platform and the top platform.

In a second embodiment, a device is provided for the elimination or significant reduction of undesirable microorganisms from objects which contains a housing having a bottom platform, sides and a top platform. The top platform is partitioned into two essentially equal sections having a bag detachably connected to the section made of a deformable UVC fluorinated film, a bottom layer containing a support layer containing a number of perforation for allowing UVC light to pass through, and may optionally contain a layer of a UVC transparent material a bottom layer made from UVC transparent quartz, and sidewalls, with a UVC absorbent liquid contained in the top platform between the top layer and the bottom layer. The device has one or more UVC emitting devices situated in the housing, between the bottom platform and the top platform.

In each of the above embodiments a device for removing debris may be attached to the housing.

In each of the above embodiments the viscosity of the UVC absorbing liquid is between about 1 to about 500 centipoises.

In each of the above embodiments the optional UVC transparent layer of the bottom layer is at least one of UVC transparent film, quartz, glass or plastic.

In each of the above embodiments the top layer may further contain sections that block UVC radiation allowing a selected area that allows UVC through.

In each of the above embodiments, the device ay further contain at least one of a timer, light switch, radiation monitor, signal lights or pressure switch.

In each of the above embodiments there may be support structures to support the top platform.

DETAILED DESCRIPTION OF THE DISCLOSURE

As used herein the term UVC refers to electromagnetic radiation with wavelengths ranging between 200-280 nanometers, inclusively.

As used herein the terms fluoropolymer, fluorinated film and perfluoro polymer films refer to materials that contain fluorine atoms bonded to carbon in the polymer and/or film.

As used herein the term absorbent refers to the property of a material that prevents at least 85% of the specific radiation wavelength from being transmitted at a chosen thickness of the material.

Also as use herein, when discussing a layer that is transparent to UVC radiation, it is meant to describe materials which allow UVC radiation to pass through without restriction to the amount or percentage of the radiation which is allowed through. In practice the amount of radiation allowed through and the amount of time the UVC radiation is allowed to pass through determines the efficiency of sanitization. A layer that lets through 25% UVC light will require a longer time of exposure compared to a layer that allows 50% of the UVC radiation through.

Figure 1:
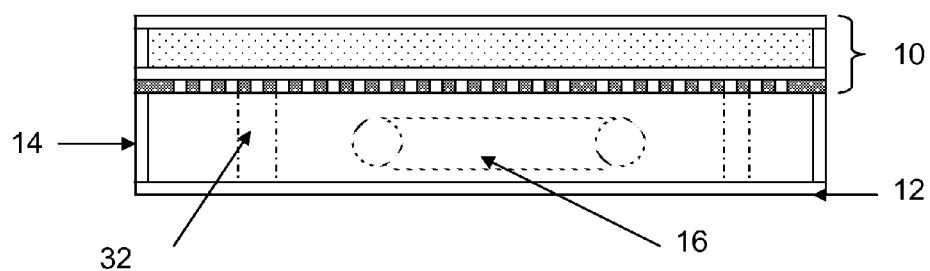
FIG. 1 is a side view of one of the exemplary embodiments showing the top platform, the bottom platform and the sidewalls of the device.
Figure 2:
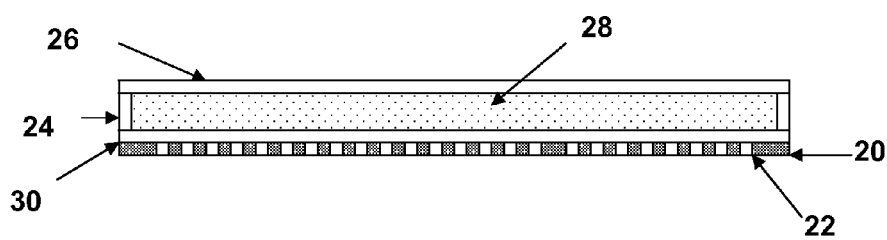
FIG. 2 is a cross sectional view of only the top platform showing the top layer 26, the bottom layer 20, perforations in the bottom layer 22 and the UVC absorbing liquid 28.
Figure 3:
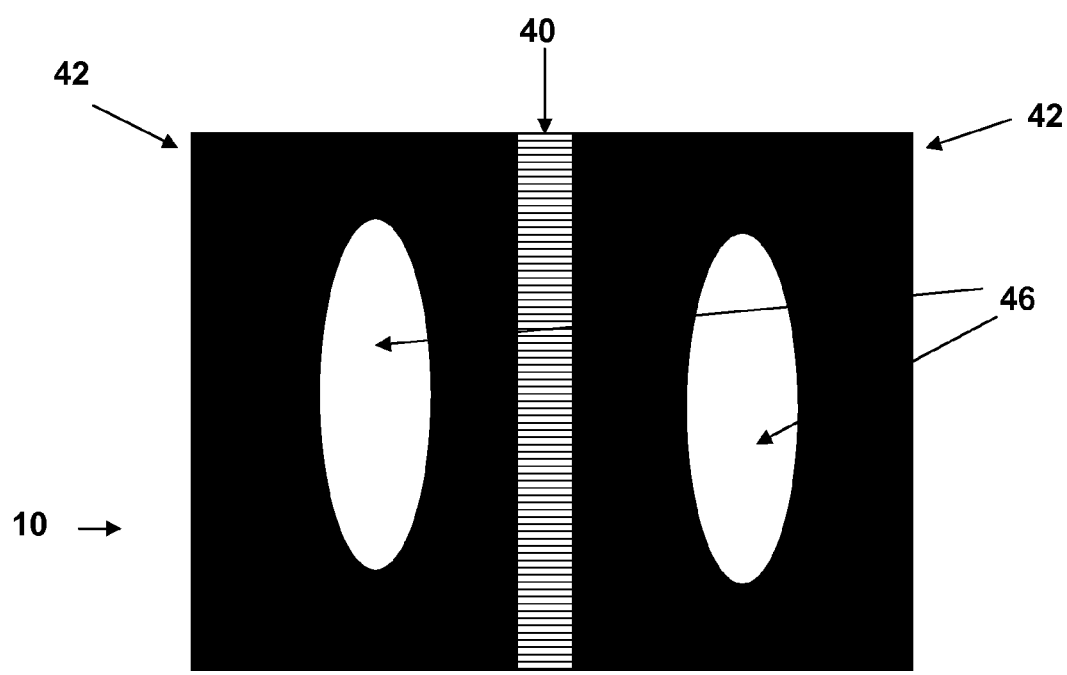
FIG. 3 shows a top view of the top layer of the top platform including the partition 40, areas that are impervious to UVC radiation 42 and areas which are transparent to UVC radiation 46.

FIG. 1 shows an exemplary embodiment of the current disclosure of a top platform 10, a bottom platform 12, and sidewalls 14, and one or more UVC emitting lamps 16. The housing bottom platform and the sidewalls may be made from any of a number of structural materials well known in the art including, for example, plastic, metal, wood and other structural material. The one or more UVC lamps 16 predominantly emit a wavelength of 254 nm. The sidewalls could be vertical or could be slanted in or out depending on the desired design of the device. The device may be of any desirable geometric shape including, for example, circular, oval, square, rectangular, triangular or other polygonal shape.

The most effective wavelength for killing or inactivating microorganisms is the 100-290-nm range, which is the UVC wavelength band. It is composed of short wavelengths from 200 to 280 nm. Most commercially available UVC lamps are low pressure mercury vapor lamps that give off a wavelength of 254 nm, which is near the optimum for killing or inactivating microorganisms. Low-pressure mercury-vapor lamps usually are made with a quartz bulb in order to allow the transmission of short wavelength light. Natural quartz allows the 254 nm wavelength to pass through but blocks the 184 nm wavelength. Synthetic quartz may also be used which allows the 184 nm wavelength to pass, however 184 nm can produce ozone. The lamps are generally doped with materials that suppress or eliminate the 184 nm wavelengths in low-pressure mercury vapor lamps.

Not to be held to theory, a wavelength of 254 nm UV will break down the molecular bonds within the DNA of microorganisms producing thymine dimers in their DNA thereby destroying them, rendering them harmless or prohibiting growth and reproduction. It is a process similar to the UV effect of longer wavelengths UVB on humans. However UVB and UVA do not act as sanitizing radiations.

As an example, commercially available T5 size UVC germicidal lamps range in input power from about 7-16 watts for a tube which is 11.3 inches long. Output wattage for these lamps, consisting primarily of 254 nm emissions, is approximately 2-4 watts with an efficiency rating of between about 20 and about 40 $\mu W/cm^2$ at a distance of 1 meter from the tube.

Power intensity of approximately 1400 to 2800 µW/cm² measured at a distance of 2 inches from the bulb surface is achieved.

Again not to be held to theory, it has been reported that to reach a 99% kill rate of bacillus anthracis a dosage of 8,700 µW second/cm² is required. Thus, in the current example and using the equation: Intensity X Exposure Time=$\mu W$ second/$cm^2$, a lamp with a minimum power intensity of 1400 $\mu/cm^2$ at 2 inches from the bulb surface, an exposure time of less than 7 seconds is required. Of course a longer time will improve the kill rate for bacillus anthracis. Other notable 99% kill rate exposure requirements for UVC (measured in $\mu W/cm^2$) are: *E-coli*=6500, *Salmonella typhosa*=6000, Dysentery=4200 and Cholera=6500. It should be noted that in the example a 7 second exposure would be sufficient to provide a 99% kill rate of all the aforementioned bacteria. Viruses are also killed by UVC, some of the toughest being poliovirus and rotavirus, which require 21,000 $\mu W/cm^2$ for a 99% kill rate. Thus using the lamps of the above example, a 15 second exposure would provide a 99% kill rate. Also molds and yeasts can be killed by UVC exposure.

FIG. 2 shows the top platform 10 of an exemplary embodiment of the disclosure, a bottom support layer of the platform 20, containing perforations 22, sidewalls 24, a top layer 26, an optional UVC transparent layer 30, and a reservoir of UVC absorbing liquid 28.

A switch may be optionally a part of the device which turns the UVC lamp or lamps on when pressure is applied to the top platform. The switch also turns off the UVC lamp when pressure is removed. There may optionally be a time delay between when the switch becomes depressed and when the lamp is turned on, such delays allows the top platform to become closed and the UVC absorbing liquid to flow around the areas which as not intended to be transparent to the UVC emission. A signal light may be included which alerts the user that the device has been activated and that the UVC lamps are emitting radiation, the signal light also alerting the user when the lights are turned off and that it is safe to remove the object being sanitized. The signal light may also be an auditory signal. Sensors may also be present which would measure the amount of UVC energy emitted when the lamp(s) are engaged thus measuring a desired amount of radiation. The sensor may be tied to a control which can shut the lights off after a desired level of radiation is obtained.

The top platform 10 is transparent to 254 nm radiation so that any object placed on top of the top layer 26 will receive the desired dosage of radiation. The top layer 26 is deformable so that, in operation when pressure is applied, the top layer will push the liquid aside and reach the bottom layer 20. The top layer 26 may be any of the films that are mechanically tough to withstand repeated wear and that are transparent to UVC radiation. Typical materials are the perfluoro polymer films available from DuPont® such as Teflon® and FEP (fluorinated ethylene propylene) films. As Teflon® becomes thicker its appearance becomes "milky" to visible light. FEP films are clearer films than Teflon® and are less presupposed to scattering. The films are mechanically tough and stretchable and can readily be adapted for manufacturing of the current device.

The bottom layer 20 has the strength to withstand the weight of an object such as a person standing on the device, such as, for example, 300 or more pounds. It has surprisingly been found that Plexiglas, polymethylmethacrylate, which has been described previously, can withstand 300 or more pounds but is not suitable for sanitization application since Plexiglas absorbs the UVC wavelengths which are need to kill the microorganisms of interest. Some specialty polymer films such as high-performance amorphous ethylene copolymer are 20% transparent to UVC at a thickness of 2 mm. However in order to be used in a support layer the thickness needs to be significantly larger. According to such physical laws as the Beers-Lambert law the absorbance of a material increases proportionally to the thickness of the material, and by association the transmittance decreases. Normal glass, such as plate glass or borosilicate glass, can not be used in the devices designed to be sanitizing devices as they block essentially all of the useful UVC radiation. Research has found that quartz is a suitable material for the device. When thick enough quartz can withstand 300 or more pounds and is over 95% transparent to UVC radiation. A support layer 20 may be positioned under the quartz bottom layer of the top platform. The support layer is perforated to allow the UVC light to pass through. The thickness of the support layer is selected to add strength to the top platform and allow for a reduction in the thickness of quartz bottom layer. The support layer may be configured for example, as a honeycomb or open crosshatch and be for example, 1 cm thick. The thickness of the mesh support may vary depending on the amount of weight the device is required to support. The mesh layer is designed to optimize the amount of UVC radiation passed through it and onto the surfaces to be sanitized. Because of the ability of the support layer to hold a large amount of weight, UVC transparent films, glass, Plexiglas, polymer films and plastic layers 30 may be used, provided they are thin enough to allow UVC radiation to pass through.

Other support mechanisms are herein disclosed such as, for example, support posts or beams which can be attached to the center partition, 32 in FIG. 1.

FIG. 3 depicts a top view of the top layer of the top platform, 10, showing the petition, 40, sections in the top layer that block UVC radiation, 42, and areas that allow UCV radiation to come through, 46. The areas that allow UVC light to shine through can be any desired size and shape limited only by the size of the sections defined by the partition and sidewalls of the top platform.

The UVC absorbing material 28 is any liquid which can readily flow when pressure is applied and which essentially absorbs UVC radiation. The liquid is between 1 and 500 centipoise which will allow it to flow when either pressure is applied or when gravity causes it to flow. Materials such as silicon fluids are suitable as the UVC absorbing liquid.

The top platform may include removable bags 50, as shown in FIG. 4, made from UVC transparent fluoropolymers including, for example, Teflon® and FEP film available from DuPont. The bag can be removable attached to the structure of the top platform as depicted by attachment points 52, in FIG. 4. The bags contain the UVC absorbing liquid which again has a viscosity that allows for the liquid to move around in response to pressure and will return to its original position when the pressure is removed. A removable bag would allow for replacement of the bag when necessary, for example, in case the surface becomes scuffed and the sanitization process becomes inefficient, for example, if the UVC emission becomes absorbed or diffused away from its intended target. Also if there is a leak somewhere in the top platform a replacement bag may be used to eliminate the problem. The bag may include a means for attachment to the device and have a volume large enough to fit into the area defined by the bottom layer and the sidewalls. As an example, an exemplary bottom layer is 18" by 18" with sidewall of 0.25". The volume is thus 648 cubic inches or 1325 milliliters. A bag with dimensions of 18" long by 18" wide by 0.25" deep will hold 1325 milliliters of the UVC absorbing liquid and fit snuggly in the cavity of the top platform defined by the bottom layer and sidewall. In the case where the top platform is situated in a tilted position, the liquid will flow toward the lower end of the bag and be stored there. The bag will be flexible enough to remain attached to the sidewalls of the top platform but will deform to allow the liquid to flow into and out of the reservoir. The bag may be used either with a perforated support bottom layer alone or with a UVC transparent layer, such as for example, quartz, glass, plexiglas, polymer or plastic.

Figure 5:
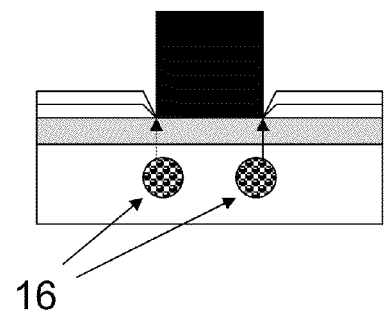
FIG. 5 shows the position of the UVC emitting devices when positioned underneath the area where the object has been places and the UVC liquid has been removed.
Figure 6:
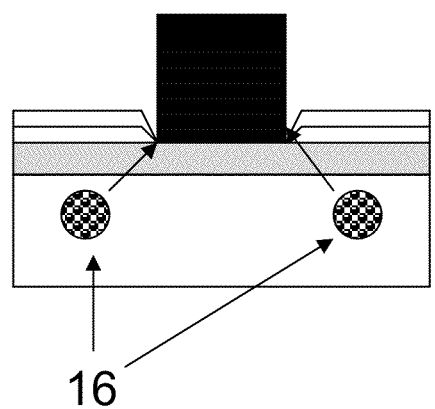
FIG. 6 shows the position of the UVC emitting devices when positioned at an oblique angle to the area where the object has been places and the UVC liquid has been removed.

The UVC lamps 16 may be situated directly under the areas object to be sanitized, FIG. 5, or they may be situated at an angle from such areas as in FIG. 6. The position of the lamps is chosen so as to allow more or less UVC light from escaping the housing.

The device may include a cleaning surface such as for example, a mat, a cloth or anther area which is designed to remove dirt, duct and any debris that might hinder the UVC emission from exposing the surface of the object intended for sanitizing.

The device may further comprise a flap attached to the outside of the sidewalls of the top platform to help prevent any extraneous UVC radiation from escaping.

An object to be sanitized is placed on the top surface of the top platform of the device and the pressure of the object, or an auxiliary pressure such as, for example, when a person holding the object presses down on the object, enough pressure is applied to cause the UVC absorbing liquid to flow away from these pressure areas allowing the top layer to either fully or partially coming into contact with the quartz glass bottom layer. A switch may turn the UVC lamps on allowing the sanitizing radiation to pass through the bottom layer and the fluoropolymer top layer to expose the bottom of the object and thereby cause microorganisms to be killed to a desire preselected level. An optional sensor residing inside the housing, upon which the UVC light directly impinges, may measure the dosage of radiation and shut off the lamps when the desired dosage has been reached. An optional indicator light may turn on when the UVC lamps are turned on, or make a noise if an auditory signal device is present, and the light turn off when the UVC lamps are turned off.

Figure 4:
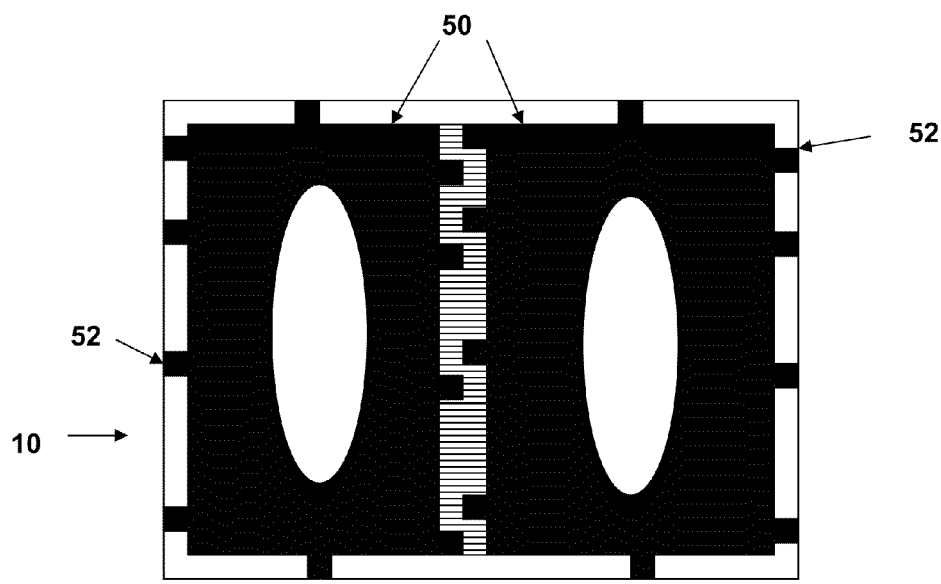
FIG. 4 shows a top view of the top layer of the top platform including removable bags 50 and tabs 52, for attaching the bags to the frame of the top platform.

The top platform of the invention may not contain any UVC transparent layers at all. In this case the perforated support layer is the sole bottom layer of the top platform and has the same characteristics as aforementioned. A removable bag, as shown in FIG. 4, made from UVC transparent fluoropolymers including, for example, Teflon® and FEP film available from DuPont is positioned on top of the support layer. The perforations of the support layer are designed and situated to allow the bag film material to span the opens in the support layer.

The aforementioned pressure can be applied by way of stepping on the top platform, placing one's hands on the platform or placing an object on the platform such that the top platform reaches a horizontal position. When the platform reaches a horizontal position, the housing obtains an enclosed configuration such that radiation emitting from the UVC emitting lamp can not escape. The only places which are exposed to UVC radiation are the areas where the pressure was applied. As a further protection against escaping UVC radiation, a UVC absorbing flap may optionally be attached to the sides of the top platform extending downward so that when pressure is applied to the top platform and it reaches a horizontal position to enclose the UVC lamp, the flats extend below the junction of the top platform and the sides of the housing.

Objects that may be sanitizing by the current devices and methods includes bags, handbags, purses, footwear or other objects, as well as bare feet, hands, paws, hooves or other anatomical surfaces. The devices and methods are also suitable for house pets and farm animals such as horses.

What is claimed is:

1. A device for sanitizing objects, comprising:
    a) a housing comprising a bottom platform, sidewalls that enclose the sides of the housing and a top platform that encloses the top of the housing and is structurally attached to the housing, the top platform comprising:
        i) a bottom layer comprising a support layer comprising perforations which allow UVC light to pass through into the top platform;
        ii) a UVC transparent layer on top of the bottom layer of at least one of a UVC transparent film, quartz, glass or plastic;
        iii) sidewalls that enclose the top platform,
        iv) a partition aligned from one sidewall of the top platform to the opposite sidewall of the top platform dividing the top platform into two essentially equal sections,
        v) a UVC transparent fluorinated film in addition to the UVC transparent layer in the form of a bag capable of being filled with the UVC absorbent fluid, wherein the bag can be positioned inside the volume of each section defined by the bottom layer, the sidewalls and partition of the top platform, wherein the bag is capable of being removably attached to the top platform, and wherein the UVC absorbent fluid having a viscosity range between about 1 and about 500 centipoises is situated between the top layer film and the bottom layer, the amount of the fluid chosen to provide a selected thickness;
    b) a UVC emitting device positioned between the bottom platform and the bottom layer of the top platform, and
    c) optionally a device adjacent to the housing for removing debris.

2. The device of claim 1, wherein the bag is defined by a top and a bottom layer and wherein the top layer of the bag comprise sections that block UVC radiation allowing a selected area that allows UVC through.

3. The device of claim 2, further comprising at least one of a timer, light switch, radiation monitor, signal lights or pressure switch.

* * * * *